(12) United States Patent
Blattner et al.

(10) Patent No.: US 9,902,965 B2
(45) Date of Patent: Feb. 27, 2018

(54) BACTERIA WITH IMPROVED METABOLIC CAPACITY

(71) Applicant: SCARAB GENOMICS, LLC, Madison, WI (US)

(72) Inventors: Frederick R. Blattner, Madison, WI (US); David A. Frisch, Fitchburg, WI (US); Robert E. Novy, Verona, WI (US); Terrance M. Henker, Madison, WI (US); Eric A. Steffen, Mount Horeb, WI (US); Jose A. Sanchez, Beer Creek, WI (US); Christopher R. Blattner, Madison, WI (US); Hyunsic Choi, Madison, WI (US); Gyorgy Posfai, Szeged (HU)

(73) Assignee: SCARAB GENOMICS, LLC, Madison, WI (US)

(*) Notice: Subject to any disclaimer, the term of this patent is extended or adjusted under 35 U.S.C. 154(b) by 0 days.

(21) Appl. No.: 15/036,376

(22) PCT Filed: Nov. 13, 2014

(86) PCT No.: PCT/US2014/065545
§ 371 (c)(1),
(2) Date: May 12, 2016

(87) PCT Pub. No.: WO2015/073720
PCT Pub. Date: May 21, 2015

(65) Prior Publication Data
US 2016/0298126 A1 Oct. 13, 2016

Related U.S. Application Data

(60) Provisional application No. 61/904,298, filed on Nov. 14, 2013.

(51) Int. Cl.
| | |
|---|---|
| C12N 1/20 | (2006.01) |
| C12N 15/00 | (2006.01) |
| C12P 21/06 | (2006.01) |
| C07H 21/04 | (2006.01) |
| C12N 15/70 | (2006.01) |
| C12N 9/10 | (2006.01) |
| C12R 1/19 | (2006.01) |

(52) U.S. Cl.
CPC ............ *C12N 15/70* (2013.01); *C12N 9/1022* (2013.01); *C12N 9/1048* (2013.01); *C12R 1/19* (2013.01); *C12Y 202/01006* (2013.01); *C12Y 204/00* (2013.01)

(58) Field of Classification Search
None
See application file for complete search history.

(56) References Cited

U.S. PATENT DOCUMENTS

| | | |
|---|---|---|
| 2008/0009041 A1 | 1/2008 | Mizoguchi et al. |
| 2009/0104667 A1 | 4/2009 | Asukura et al. |
| 2011/0111458 A1 | 5/2011 | Masuda et al. |
| 2013/0011874 A1 | 1/2013 | Campbell et al. |
| 2013/0210097 A1 | 8/2013 | Dischert et al. |

FOREIGN PATENT DOCUMENTS

WO WO-2009105551 * 8/2009

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Kisselev L., Polypeptide release factors in prokaryotes and eukaryotes: same function, different structure. Structure, 2002, vol. 10: 8-9.*
International Search Report of PCT/US2014/065545 dated Feb. 25, 2015.
Written Opinion of PCT/US2014/065545 dated Feb. 25, 2015.
Hayashi, K., et al., "Highly accurate genome sequences of *Escherichia coli* K-12 strains MG1655 and W3110," Molecular Systems Biology, vol. 2, Issue 1, pp. 1-5 (Feb. 21, 2006).
Kuhnert, P., et al., "Rapid and Accurate Identification of *Escherichia coli* K-12 Strains," Applied and Environmental Microbiology, pp. 4135-4139 (Nov. 1995).
Posfai, Gyorgy, et al., "Emergent Properties of Reduced-Genome *Escherichia coli*," Science, vol. 312, pp. 1044-1046, (May 19, 2006).

* cited by examiner

*Primary Examiner* — Iqbal H Chowdhury
(74) *Attorney, Agent, or Firm* — Polsinelli PC; Christopher M. Cabral (57) ABSTRACT

*E. coli* bacteria comprising genetic modifications to enhance fermentability and production of protein and nucleic acids are provided.

19 Claims, 3 Drawing Sheets

SEQUENCE LISTING

<160> NUMBER OF SEQ ID NOS: 22

<210> SEQ ID NO 1
<211> LENGTH: 26
<212> TYPE: DNA
<213> ORGANISM: Artificial Sequence
<220> FEATURE:
<223> OTHER INFORMATION: PCR primer

<400> SEQUENCE: 1
aatggtgatg ttggtgttta cgctgc                                      26

<210> SEQ ID NO 2
<211> LENGTH: 42
<212> TYPE: DNA
<213> ORGANISM: Artificial Sequence
<220> FEATURE:
<223> OTHER INFORMATION: PCR primer

<400> SEQUENCE: 2
gcatctgtgg taaaaaccct cgatacattg cggagaaaaa tt                    42

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
gccccagcgc acagttcagg                                             20

<210> SEQ ID NO 4
<211> LENGTH: 44
<212> TYPE: DNA
<213> ORGANISM: Artificial Sequence
<220> FEATURE:
<223> OTHER INFORMATION: PCR primer

<400> SEQUENCE: 4
aatgtatcga gggtttttac cacagatgcg tttatgccag tatg                  44

<210> SEQ ID NO 5
<211> LENGTH: 37
<212> TYPE: DNA
<213> ORGANISM: Artificial Sequence
<220> FEATURE:
<223> OTHER INFORMATION: PCR primer

<400> SEQUENCE: 5
atgaactagt tgtgattcgc catctttata ttgagcg                          37

```
<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
atgagattct ccaccagcgc tttggtggac                              30

<210> SEQ ID NO 7
<211> LENGTH: 34
<212> TYPE: DNA
<213> ORGANISM: Artificial Sequence
<220> FEATURE:
<223> OTHER INFORMATION: PCR primer

<400> SEQUENCE: 7
gctcatacta gtgcgcctgc gtctgattgt gttg                         34

<210> SEQ ID NO 8
<211> LENGTH: 43
<212> TYPE: DNA
<213> ORGANISM: Artificial Sequence
<220> FEATURE:
<223> OTHER INFORMATION: PCR primer

<400> SEQUENCE: 8
gtttcaagcc ggagatttca atatgaaacc atatcagcgc cag               43

<210> SEQ ID NO 9
<211> LENGTH: 34
<212> TYPE: DNA
<213> ORGANISM: Artificial Sequence
<220> FEATURE:
<223> OTHER INFORMATION: CTTACGAAGCTTCGGCATATGGGAGCGGACTTTG

<400> SEQUENCE: 9
cttacgaagc ttcggcatat gggagcggac tttg                         34

<210> SEQ ID NO 10
<211> LENGTH: 43
<212> TYPE: DNA
<213> ORGANISM: Artificial Sequence
<220> FEATURE:
<223> OTHER INFORMATION: PCR primer

<400> SEQUENCE: 10
ctgatatggt ttcatattga atctccggc ttgaaacaaa tgt                43

<210> SEQ ID NO 11
<211> LENGTH: 26
<212> TYPE: DNA
<213> ORGANISM: Artificial Sequence
<220> FEATURE:
<223> OTHER INFORMATION: PCR primer

<400> SEQUENCE: 11
ctcgcgcatc tgctcaatca acactt                                  26

<210> SEQ ID NO 12
<211> LENGTH: 27
<212> TYPE: DNA
<213> ORGANISM: Artificial Sequence
<220> FEATURE:
<223> OTHER INFORMATION: PCR primer
```

<400> SEQUENCE: 12
gaaaaggaac cgtcgcgagg aaatact                                             27

<210> SEQ ID NO 13
<211> LENGTH: 38
<212> TYPE: DNA
<213> ORGANISM: Artificial Sequence
<220> FEATURE:
<223> OTHER INFORMATION: PCR primer

<400> SEQUENCE: 13
ctgctaacta gtgcggctat cggttatgct cgtgctac                                 38

<210> SEQ ID NO 14
<211> LENGTH: 43
<212> TYPE: DNA
<213> ORGANISM: Artificial Sequence
<220> FEATURE:
<223> OTHER INFORMATION: PCR primer

<400> SEQUENCE: 14
ctgccagtca tattgattta acggctgctg taatgctggt aac                           43

<210> SEQ ID NO 15
<211> LENGTH: 35
<212> TYPE: DNA
<213> ORGANISM: Artificial Sequence
<220> FEATURE:
<223> OTHER INFORMATION: PCR primer

<400> SEQUENCE: 15
ggcatagaag cttgctcagg cgcggatttg ttgtg                                    35

<210> SEQ ID NO 16
<211> LENGTH: 43
<212> TYPE: DNA
<213> ORGANISM: Artificial Sequence
<220> FEATURE:
<223> OTHER INFORMATION: PCR primer

<400> SEQUENCE: 16
cagcagccgt taaatcaata tgactggcag caacactgcg cgc                           43

<210> SEQ ID NO 17
<211> LENGTH: 39
<212> TYPE: DNA
<213> ORGANISM: Artificial Sequence
<220> FEATURE:
<223> OTHER INFORMATION: PCR primer

<400> SEQUENCE: 17
gaatccaagc actagtcaca gcacccatta cgcaatggc                                39

<210> SEQ ID NO 18
<211> LENGTH: 46
<212> TYPE: DNA
<213> ORGANISM: Artificial Sequence
<220> FEATURE:
<223> OTHER INFORMATION: PCR primer

<400> SEQUENCE: 18
catctacaga gaaatcatac agtatcaagt gttttgtaga aattgt                        46

<210> SEQ ID NO 19
<211> LENGTH: 44

```
<212> TYPE: DNA
<213> ORGANISM: Artificial Sequence
<220> FEATURE:
<223> OTHER INFORMATION: PCR primer

<400> SEQUENCE: 19
ggccctcgag aagcttctat ggaaaaagtc gagaaacgcc tgac            44

<210> SEQ ID NO 20
<211> LENGTH: 45
<212> TYPE: DNA
<213> ORGANISM: Artificial Sequence
<220> FEATURE:
<223> OTHER INFORMATION: PCR primer

<400> SEQUENCE: 20
cacttgatac tgtatgattt ctctgtagat gatagcgaag gcgta           45

<210> SEQ ID NO 21
<211> LENGTH: 22
<212> TYPE: DNA
<213> ORGANISM: Artificial Sequence
<220> FEATURE:
<223> OTHER INFORMATION: PCR primer

<400> SEQUENCE: 21
gcctgctgcg tctggatgtt gg                                    22

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
actggttcat cccggcgttg gta                                   23
```

BACTERIA WITH IMPROVED METABOLIC CAPACITY

CROSS-REFERENCE TO RELATED APPLICATIONS

This application is the 35 U.S.C. 371 National Stage of International Application Number PCT/US2014/065545, filed Nov. 13, 2014, which claims the benefit of U.S. Provisional Application No. 61/904,298, filed Nov. 14, 2013, the contents of which are incorporated herein by reference.

SEQUENCE LISTING SUBMISSION VIA EFS-WEB

A computer readable text file, entitled "010447-5036-US-SEQ-List_ST25.txt", created on or about May 12, 2016, with a file size of about 5 KB contains the sequence listing for this application and is hereby incorporated by reference in its entirety

FIELD OF THE INVENTION

The present invention is directed to genetically modified *E. coli* K strain derivatives having improved fermentation characteristics that are particularly useful for enhanced production of nucleic acids and proteins by fermentation.

BACKGROUND OF THE INVENTION

*Escherichia coli* (*E. coli*) is a universal cloning host and is the most common organism used in the production of proteins, nucleic acids, metabolites and secondary metabolites in both research and industry. Many of the most important new drugs are manufactured by fermentation in *E. coli*, which remains the most economical and efficient platform available for production of such molecules. In particular, therapeutics addressing health problems intractable to small-molecule drugs and other traditional treatments. About one-third of all biotherapeutics are currently manufactured in *E. coli* including single-chain antibodies, which are challenging to develop as well as extremely expensive due in part to limited yields from the *E. coli* strains in which they are made. Stalled growth is a significant problem that frequently limits *E. coli* performance and product formation in high density fermentations

*E. coli* K-12 strains were instrumental in early advances in genetics and microbial physiology and continue to serve as the workhorse of molecular biology methods and techniques. *E. coli* B strains are often favored as protein expression platforms at laboratory scale, in part due to the availability of strains engineered for use with the T7 polymerase expression systems pioneered by Studier and Moffat [Studier and Moffat, J. Mol. Biol. 189:113 (1986); Studier, J. Mol. Biol. 219:37 (1991)]. At industrial scale, B strains are also recognized as having superior protein production characteristics relative to K-12 strains, even with protein expression systems other than T7 polymerase. Nevertheless, the large quantity of mobile genetic elements, such as insertion sequence elements and prophage, in these strains can cause production problems under stress, particularly the stress encountered when expressing insoluble or toxic targets. On the other hand, *E. coli* B strains are generally seen as inferior to K strains for producing plasmid DNA.

The phylogenetic relationship of *E. coli* K and B strains is quite close. To date, more than 60 diverse *E. coli* strains have been completely or at least substantially sequenced and a detailed phylogenetic map has been produced based on differences among these strains within a series of conserved genes (adk, fumC, icd, gyrB, mdh, purA and recA). All K-12 and B strains fall within a single clade in the *E. coli* phylogenetic map [Lukjancenko, Wassenaar and Ussery, Microb. Ecol. 60:708 (2010)]. All current K-12 strains are thought to derive from Charles E. Clifton's original K-12 strain (O16, $\lambda^+$, $F^+$) first isolated at Stanford University in Palo Alto in the late 1920s [Bachman, In Neidhardt, F. C., et al., *E. coli* and *S. typhimurium*: Cellular and Molecular Biology. ASM Press, Washington D.C. 1996]. Existing B strains derive largely from Felix d'Herelle's *Bacillus coli* strain (O7, $\lambda^R$, $F^-$), originally isolated at the Pasteur Institute in Paris as early as 1918 [Daegelen et al., J. Mol Biol 394:634 (2009)]. The close phylogenetic relationship between K-12 and B strains is intriguing from an historical perspective. However, recent advances in our understanding of bacterial evolution and how modern strains may have diverged from ancestral enteric bacteria calls the tidy historical relationship between K and B strains into question [Studier, et al., J. Mol. Biol. 394:653 (2009)]. Regardless, recognition of the differences between K-12 and B strains and their relative advantages for different research and industrial applications is largely based on empirical observation.

The field has long desired a single strain platform possessing superior growth and protein production characteristics of B strains with the genetic tractability and superior DNA production capabilities of K-12 strains. Such an *E. coli* strain could facilitate development of standard fermentation regimens for optimizing growth and maximizing yield across a diverse spectrum of products.

SUMMARY OF THE INVENTION

The present invention provides genetically modified *E. coli* K-12 strains with improved growth and improved production of recombinant proteins and nucleic acids in fed batch fermentations.

The *E. coli* K-12 strains are modified to (a) enhance orotate phosphoribosyltransferase activity (b) produce active acetohydroxy acid synthase II and (c) reduce expression of the iclR and arpA gene products.

In several embodiments, the present invention provides a reduced genome *E. coli* K-12 strain modified so as to (a) enhance orotate phosphoribosyltransferase activity (b) produce active acetohydroxy acid synthase II and (c) reduce expression of the iclR and arpA gene products. In one aspect, the genome of the reduced genome *E. coli* K strain has a genome that is genetically engineered to be from about 5% to about 30% smaller than the genome of its native parent strain and lacks all insertion sequences. Reduced genome bacteria may be produced by deleting selected genes from a native parental strain of a bacterium or may, for example, be entirely synthesized as an assembly of preselected genes. As is readily apparent from the discussion herein, a reduced genome bacterium has fewer than the full complement of genes found in a native parent strain to which it is compared, and with which it shares certain essential genes.

Methods for producing a polypeptide employing the modified *E. coli* K-12 strains of the invention are also provided. In one embodiment, the polypeptide is produced by culturing the modified *E. coli* K-12 strain comprising a nucleic acid encoding the polypeptide operatively linked to an expression control sequence, under conditions suitable to express the polypeptide. In one aspect, the nucleic acid encodes a heterologous protein. In a related aspect, the protein is produced in the modified *E. coli* strains of the invention at a higher level than in an *E. coli* K-12 strain that does not comprise the modifications described herein. In still another aspect protein production is increased at a higher level than from an *E. coli* K-12 strain that does not comprise the modifications described herein by virtue of the higher cell numbers such modified cells can attain under the same growth conditions.

Methods for amplifying heterologous nucleic acids (e.g. a vector such as plasmid) employing the modified *E. coli* K-12 strains of the invention are also provided. In one embodiment, the nucleic acid is produced by culturing the modified *E. coli* K strain comprising the heterologous nucleic acid under suitable nutrient conditions, thereby amplifying the nucleic acid. In still another aspect nucleic acid production is increased at a higher level than from an *E. coli* K-12 strain that does not comprise the modifications described herein by virtue of the higher cell numbers such modified cells can attain under the same growth conditions.

These and other embodiments of the present invention are described in more detail herein below.

DESCRIPTION OF THE DRAWINGS

In FIG. 1, intrinsic growth rate (x axis) and maximum fermentation OD (fermentability i.e. fermentation productivity) (y axis) are plotted with isogenic pairs (strains with the same genetic background aside from the modifications) shown connected by arrows. T69 is MDS69, a multiple deletion strain which comprises all the deletions of MDS42 and twenty-seven additional deletions. Note the lack of absolute correlation between the intrinsic growth rate under standard conditions and the fermentability. In some examples, strains with higher fermentability exhibit lower intrinsic growth rate. Genome modifications to achieve higher growth rate may not necessarily result in better production strains (i.e. increased target yield) and thus must be empirically tested.

FIG. 2 illustrates three parallel fermentations (#105, #102 and #98) performed at 10 L scale in Korz minimal medium (Korz D J et al., J. Biotechnol., 39(1):59-65 (1995)) fed with glucose via a computer controlled pump. *E. coli* MDS69recA(meta) carrying a plasmid carrying an IPTG inducible promoter expressing a test protein upon induction with IPTG was grown in 21 hrs to $OD_{600}$ of 250-300 by means of a 7 hour batch phase followed by a 14 hr. exponential glucose feed at mu of 0.3 $hr^1$. Then IPTG was added to 75 micromolar and the feed was adjusted to three different constant production feed rates as indicated. $OD_{600}$ is plotted along the left y axis on the logarithmic scale and time along the x axis. Product formation in grams per liter in the fermenter (linear scale on right y axis) is plotted for the 20 to 48 hours post induction time period. Product was measured by scanning gels vs. a BSA standard, for example, the inset gel photograph showing product formation at the indicated time points is for fermentation no. 105, the maximum feed rate tested. After induction, the cell mass remains metabolically active and production continues for many hours achieving very high product levels and OD does not drop.

FIG. 3. At the end of fermentation no. 105, cell viability was assessed using a LIVE/DEAD® BacLight™ Bacterial Viability Kit (LifeTechnologies, Grand Island, N.Y. 14072) followed by microscopic examination (FIG. 3). The assay shows almost no dead cells and no cell lysis was observed. This, coupled with increasing yield of the target protein, confirms that target protein induction redirects cellular resources that were previously devoted only to cell growth to the target production. Specifically, bacterial cells were treated with Baclight™ reagent for 15 minutes and then imaged using a Leica DMI 3000 fluorescent microscope. Cells stained with either propidium iodide (green, left panel) or SYTO 9 (red, right panel) indicated live or dead cells, respectively. Percent live cells was greater than 99%. Fed-batch fermentation was for 26 hours in Korz minimal media.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed by such values. This includes ranges that can be formed that do or do not include a finite upper and/or lower boundary. This also includes ratios that are derivable by dividing a given disclosed numeral into another disclosed numeral. Accordingly, the skilled person will appreciate that many such ratios, ranges, and ranges of ratios can be unambiguously derived from the data and numbers presented herein and all represent various embodiments of the present invention.

A "reduced genome" bacterium as used herein means a bacterium having about 1% to about 75% of its genome (e.g. protein coding genes) deleted, for example about 5%, about 10%, about 20%, about 30% about 40%, about 50% or about 60% of the genome deleted. In one embodiment, the reduced genome bacteria used in the practice of the present invention have a genome that is preferably genetically engineered to be at least two percent (2%) and up to twenty percent (20%) (including any number therebetween) smaller than the genome of a native parent strain. Preferably, the genome is at least five percent (5%) and up to thirty percent (30%) smaller than the genome of a native parent strain. More preferably, the genome is eight percent (8%) to fourteen percent (14%) to twenty percent (20%) (including any number therebetween) or more smaller than the genome of the native parent strain. Alternatively, the genome may be engineered to be less than 20%, less than 30%, less than 40% or less than 50% smaller than the genome of a native parental strain. The term "native parental strain" means a bacterial strain found in a natural or native environment as commonly understood by the scientific community to represent the foundation of a strain line and on whose genome a series of deletions can be made to generate a bacterial strain with a smaller genome. Native parent strain also refers to a strain against which the engineered strain is compared and wherein the engineered strain has less than the full complement of the native parent strain. The percentage by which a genome has become smaller after a series of deletions is calculated by dividing "the total number of base pairs deleted after all of the deletions" by "the total number of base pairs in the genome before all of the deletions" and then multiplying by 100. Similarly, the percentage by which the genome is smaller than the native parent strain is calculated by dividing the total number of nucleotides in the strain with the smaller genome (regardless of the process by which it was produced) by the total number of nucleotides in a native parent strain and then multiplying by 100.

In one embodiment, a "reduced genome" bacterium means a bacteria for which removal of the above amounts of genome does not unacceptably affect the ability of the organism to grow on minimal medium. Whether removal of two or more genes "unacceptably affects" the ability of the organism to grow on minimal medium in the present context depends on the specific application. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about fifteen minutes to about three hours. Non-limiting examples of suitable reduced genome bacteria, as well as methods for deleting DNA from a bacterium such as *E. coli*, are disclosed in U.S. Pat. Nos. 6,989,265, 7,303, 906, 8,119,365, 8,039,243 and 8,178,339, each of which is hereby incorporated by reference herein.

The term "b number" used herein refers to the unique ID assigned to each gene of the K-12 MG1655 strain as described in Blattner et al., Science 277:1453-1474 (1997).

In several embodiments, an *E. coli* K-12 strain bacteria is provided that has been genetically modified so as to (a) enhance orotate phosphoribosyltransferase activity (b) produce active acetohydroxy acid synthase II and (c) reduce expression of the iclR and arpA gene products. It has been found that *E. coli* K strain bacteria comprising this combination of modifications exhibit substantially improved fermentability (i.e. fermentation productivity) and growth characteristics compared to *E. coli* K-12 strain bacteria with the same genetic background but without this combination of modifications. The modified *E. coli* K strain bacteria are surprisingly useful for producing protein and propagating nucleic acids particularly when grown in minimal media.

*E. coli* orotate phosphoribosyltransferase, an enzyme that catalyzes synthesis of pyrimidine nucleotides, is encoded by the pyrE gene, b-number b3642. The pyrE gene is present in an operon with the rph gene which encodes Ribonuclease PH, a divalent cation- and phosphate-dependent tRNA processing enzyme. The rph gene (b3643) is located upstream of pyrE. The pyrE gene is expressed at sub-optimal levels in *E. coli* K-12 strains such as MG1655 and W3310 due to a −1 frame shift mutation in the coding region of the rph gene that truncates transcription and causes a polar expression defect of the downstream pyrE gene. This mutation was originally described in Jensen, J. Bacteriol. 175:3401 (1993). U.S. Pat. No. 8,293,505, the contents of which are incorporated herein by reference, describes the production of L-amino acids in microorganisms with enhanced orotate phosphoribosyltransferase activity. Any of the methods described in U.S. Pat. No. 8,293,505 for enhancing orotate phosphoribosyltransferase may be used to create the modified *E. coli* K-12 strain bacteria of the invention. Representative examples of *E. coli* K-12 strains possessing an rph frameshift mutation that can be corrected to produce the modified *E. coli* K-12 strain bacteria of the invention include *E. coli* K-12 strain MG1655, *E. coli* K-12 strain CR63, *E. coli* K-12 strain K, *E. coli* K-12 strain W33450, *E. coli* K-12 strain W3623, *E. coli* K-12 strain 594, *E. coli* K-12 strain IAM1264, and *E. coli* K-12 strain W3110.

Enhanced orotate phosphoribosyltransferase activity in the modified *E. coli* K-12 strain of the invention corresponds to an increase in the number of orotate phosphoribosyltransferase molecules per cell compared to that of the wild type (e.g. MG1655) or unmodified strain, or to an increase in the orotate phosphoribosyltransferase activity within a cell compared to that of cells of the wild type or unmodified strain. Enhanced orotate phosphoribosyltransferase activity can be assessed by measuring the specific activity of orotate phosphoribosyltransferase produced by the bacteria, e.g. by the enzymatic assay described in Schwartz, M. and Neuhard, J. Bacteriol. 121:814-822 (1975) or the method of Poulsen et al., Eur. J. Biochem., 135:223-229 (1983). *E. coli* K-12 strains with the rph frameshift mutation produce orotate phosphoribosyltransferase activity of about 5-20 units, whereas *E. coli* strains with a wild type rph gene (without the frameshift mutation) exhibit orotate phosphoribosyltransferase specific activity levels of about 30-90 units. Preferably, modified *E. coli* K-12 strains of the invention exhibit an orotate phosphoribosyltransferase specific activity of at least about 30 units.

In several aspects, orotate phosphoribosyltransferase activity can be enhanced by a modification that increases the expression of the encoding gene relative to a parent strain such as a wild type strain or an unmodified strain otherwise having the same genetic background. The nucleotide sequence of the *E. coli* K12 strain rph-pyrE operon is described at SEQ ID NO: 11 of U.S. Pat. No. 8,293,505, incorporated herein by reference. The coding region of rph corresponds to nucleotides 1 to 687 and the coding region of pyrE corresponds to nucleotides 782 to 1423 of SEQ ID NO: 11. The −1 frameshift mutation occurs at the 3' end of the rph gene between the 667th and 671st positions of SEQ ID NO: 11 and results in a decrease in translation of the pyrE gene product.

In one aspect, the *E. coli* K-12 strain can be genetically engineered to replace the native rph gene sequence with the sequence of an rph gene from an *E. coli* strain that does not contain the −1 frameshift mutation. For example, the rph of *E. coli* K-12 Q13 and *E. coli* K-12 30(E+) strains possess an rph gene that does not contain the frameshift mutation. Additionally, the nucleotide sequence of the wild type rph-pyrE operon (without the frameshift mutation) is available from GenBank/EMBL under accession numbers X00781 and X01713.

In another aspect, orotate phosphoribosyltransferase activity can be enhanced by introducing a mutation that counteracts (i.e. complements) the native −1 frameshift mutation in the coding region of the rph gene. For example, a +1 or a −2 mutation can be introduced into the region downstream of the 3' end of the rph gene and upstream of the pyrE gene, such as insertion of a single nucleotide between the 670 and 671 positions. In a related aspect, orotate phosphoribosyltransferase activity can be enhanced by a deletion in the region upstream of the attenuator that has the effect of correcting the frameshift and bringing the coding region of rph closer to the translation initiation site of pyrE. For example, the nucleotide sequence of 610 to 691 of SEQ ID NO: 11 of U.S. Pat. No. 8,293,505 can be deleted; the resulting nucleotide sequence of the rph-pyrE operon is described at SEQ ID NO: 14 of U.S. Pat. No. 8,293,505. In still another aspect, orotate phosphoribosyltransferase activity can be enhanced by a deletion that entirely removes the rph coding sequence to bring the promoter of the rph-pyrE operon closer to the translation initiation site of pyrE. In this embodiment nucleotides 1 to 687 of SEQ ID NO: 11 of U.S. Pat. No. 8,293,505 are deleted. Surprisingly, deletion of the entire rph coding region has no deleterious effect on cell growth or viability.

Acetohydroxy acid synthases catalyze the earliest steps in the synthesis of branched-chain amino acids in bacteria. Three isozymes of acetohydroxy acid synthase exist in *E. coli*: acetohydroxy acid synthases I, II and III. *E. coli* acetohydroxy acid synthase II normally consists of a large subunit, encoded by the ilvG gene and a small subunit, encoded by the ilvM gene (b3769). The ilvG sequence of *E. coli* K-12 strain MG1655 is corrupted and is actually a pseudo gene (b-number b4488), as set forth in GenBank Accession No. AAC77488.1. The ilvG pseudo gene is comprised of two separate coding sequences, ilvG_1 (b3767) and ilvG_2 (b3768). The ilvG pseudo gene sequence in K-12 strains such as MG1655 comprises a deletion of nucleotides GT at positions 983 and 984 relative to the intact ilvG genes found in other *E. coli* strains (e.g. B strain, O strain, etc.). The deletion of these nucleotides results in a frameshift mutation and nucleotides TGA at positions 982-984 of the K-12 ilvG pseudo gene sequence serve as a premature termination codon resulting in a truncated form of ilvG corresponding to ilvG_1. Thus, the normal gene product of ilvG is not expressed and acetohydroxy acid synthase II is not present in *E. coli* K-12 strains.

*E. coli* K-12 strains can be modified to produce active acetohydroxy acid synthase II by any of the methods of U.S. Pat. No. 7,300,776, the entire contents of which are incorporated herein by reference. In one aspect, the *E. coli* K-12 strain is modified so that it harbors an ilvG gene which does not have the deletion mutation (e.g. an ilvG gene with a sequence corresponding to the wild type ilvG gene sequence such as those described at SEQ ID NOs: 3 and 5 of U.S. Pat. No. 7,300,776). Alternatively, a mutation can be introduced into the ilvG pseudo gene that corrects the −2 frameshift mutation. In one aspect, GT is inserted between the T at position 982 and the G at position 983 in SEQ ID NO: 1 (corresponding to the *E. coli* K-12 ilvG nucleotide sequence) of U.S. Pat. No. 7,300,776. In another aspect any two base insertion in this region which does not introduce a stop codon can serve to shift the reading frame back into the correct frame. For example, insertion of an AT dinucleotide at position 982 will restore expression of an active acetohydroxy acid synthase II protein. In still other aspects, the *E. coli* K-12 ilvG gene can be modified to produce active acetohydroxy acid synthase II by deleting one or four nucleotides in the region upstream of positions 984 of the ilvG gene to take the TGA codon out of frame. For example, the nucleotide C at position 979 may be deleted.

The production of intact, full-length acetohydroxy acid synthase II in the modified *E. coli* K strain of the invention can be assessed e.g. by measuring the production of the protein encoded by the ilvG gene in the modified *E. coli* K-12 strain bacteria by Western blotting using antibodies. Additionally, acetohydroxy acid synthase II activity can be easily detected by the ability of *E. coli* strains to grow in the presence of excess valine without isoleucine supplementation as described in Lawther, et al., Proc. Natl. Acad. Sci. U.S.A., 78:922-925 (1981)

The iclR and arpA genes of *E. coli* K strain are adjacent genes encoding regulatory proteins that modulate expression of the glyoxylate shunt enzymes and of acetyl-CoA synthetase, respectively. The iclR (isocitrate lyase regulator) gene, b-number b4018, is described at NCBI Entrez GeneID No. 948524. The arpA (ankyrin-like regulator protein) gene, b-number b4017, is described at NCBI Entrez GeneID No. 944933. The arpA gene was found to be partially deleted in the genome sequence of B strains such as BL21DE3 and REL606 relative to the K-12 strain sequence.

*E. coli* K-12 strains can be modified to reduce expression of the iclR and arpA gene products by introducing a mutation in the coding sequence (i.e. a change of one or more nucleotides compared to the wild type sequence) e.g. by replacement, inversion, deletion or insertion of one or more nucleotides which results in reduced function or loss of function of the iclR and arpA gene products. In one aspect, a non-sense or miss-sense mutation may be introduced into the nucleic acid coding sequence whereby a codon is changed into a stop codon or whereby a codon is changed to code for a different amino acid, in either case leading to the resulting protein having reduced function or loss-of-function. In other aspects, a frame-shift mutation may be introduced such that the reading frame of the mRNA sequence is changed, resulting in a protein having different amino acid sequence and concomitantly reduced function or loss of function. In other aspects, a mutation in a regulatory sequence (e.g. promoter) may be introduced (i.e. one or more nucleotides are altered relative to the wild type sequence) such that transcription of the gene is reduced or eliminated. In a preferred aspect, the iclR and arpA genes are inactivated (i.e. rendered non-functional) by deletion of all or part of the iclR and arpA gene sequences for example by the "scarless" deletion methods described at column 8, line 45 to column 14, line 41 of U.S. Pat. No. 6,989,265.

Any parent *E. coli* K-12 strain can be modified to create the modified *E. coli* K-12 strain of the invention, including without limitation, K-12 strains such as MG1655 (ATCC No. 47076), W3110 (ATCC No. 27325) DH1, DH10B, DH5α, Invα, Top10, Top10F, JM103, JM105, JM109, MC1061, MC4100, XL1-Blue, EC100, BW2952, EC300. In one preferred embodiment, the parent *E. coli* K-12 strain is MG1655 or W3110. The nucleotide sequence of the genome of the parental *E. coli* K-12 strain may be partially or completely known. The complete genomic sequence of several *E. coli* K-12 strains is known (see e.g. Blattner et al., Science, 277:1453-74 (1997); GenBank Accession No. U00096; NCBI database, Accession No. AP009048 (W3110), EMBL Accession No. CP000948 (DH10B), EMBL Accession No. CP001637 (DH1), and EMBL Accession No. CP001396 (BW2952), each of which is incorporated herein by reference.

In a particularly preferred embodiment, the E. coli K-12 strain that is modified to create the bacteria of the invention is a reduced genome strain. The E. coli reduced genome bacterium preferably has a genome that is genetically engineered to be at least two percent (2%) and up to forty percent (40%) (including any number therebetween), such as between 5% and 30%, smaller than the genome of a native parent strain E. coli K-12 strain. The native parent E. coli K-12 strain that is genetically engineered to create the reduced genome strain (that is then further modified to create the modified E. coli K-12 strain bacteria of the invention) can be any available E. coli K-12 strain bacteria with a partially or completely known sequence. In a preferred embodiment, the native parent E. coli K-12 strain used to create the reduced genome E. coli is K-12 strain MG1655 (annotated version m56, NCBI accession no. U000961) with a genome having 4,639,674 base pairs. In another preferred embodiment, the reduced genome bacterium has a genome that is between 4.41 Mb and 3.71 Mb, between 4.41 Mb and 3.25 Mb or between 4.41 Mb and 2.78 Mb.

Various protein coding genes can be deleted to form reduced genome bacteria. In E. coli and other bacteria, a type of DNA sequence that can be deleted includes those that in general will adversely affect the stability of the organism or of the gene products of that organism. Such elements that give rise to instability include without limitation transposable elements, insertion sequences, and other "selfish DNA" elements which may play a role in genome instability. For example, insertion sequence (IS) elements and their associated transposes are often found in bacterial genomes, and thus are targets for deletion. IS sequences are common in E. coli, and all of them may be deleted. For purposes of clarity in this document, we use the term IS element and transposable element generically to refer to DNA elements, whether intact or defective, that can move from one point to another in the genome. An example of the detrimental effects of IS elements in science and technology is the fact that they can hop from the genome of the host E. coli into a plasmid during propagation for sequencing. This artifact can be prevented by deletion from the host cells of all IS elements. For a specific application, other specific genes associated with genomic instability, such as active and inactive prophages may also be deleted.

Reduced genome bacteria of the invention may also be engineered to lack, for example, without limitation, certain genes unnecessary for growth and metabolism of the bacteria, pseudo genes, prophage, undesirable endogenous restriction-modification genes, pathogenicity genes, toxin genes, fimbrial genes, periplasmic protein genes, invasin genes, lipopolysaccharide genes, class III secretion systems, phage virulence determinants, phage receptors, pathogenicity islands, RHS elements, sequences of unknown function and sequences not found in common between two strains of the same native parental species of bacterium. Other DNA sequences that are not required for cell survival can also be deleted or omitted.

Figure 1:
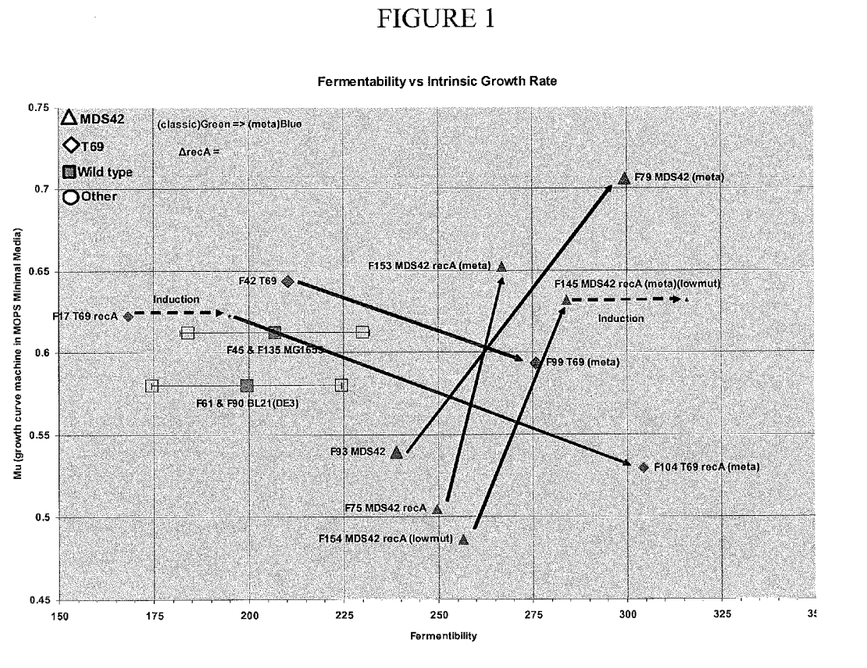
FIG. 1 illustrates the effects of metabolic mutations (correction of the rph and ilvG frameshift mutations and deletion of the iclR and arpA genes) on reduced genome *E. coli* K-12 strains (MDS42(meta), MDS42recA(meta), T69(meta) and T69recA(meta)) compared to the unmodified parent reduced genome *E. coli* K strains (MDS42, MDS42recA, T69 and T69recA) and compared to the native parent K12 strain MG1655 and B strain BL21(DE3). Growth of *E coli* in log phase follows the equation $M(t)=M(0)e^{\mu t}$ where $M(t)$ is the cell mass as a function of time in hrs, e is the base of the natural logarithms (~2.7183) and mu($\mu$), is defined as the exponential growth rate in $hr^{-1}$ Mu ($\mu$) can be measured by fitting growth curve data to this function. Intrinsic growth rate of a strain of *E coli* is mu($\mu$) measured in standard conditions such as in shake flasks at 100 rpm in Neidhardt's MOPS minimal, medium with 0.2% glucose at 37° C. in dilute culture ($OD_{600}$<1) as was done here.

In a particularly preferred embodiment, a reduced genome E. coli is provided having a genome between five percent (5%) and thirty percent (30%) smaller than the genome of a native parent E. coli K strain and lacking all insertion sequence (IS) elements and modified so as to (a) enhance orotate phosphoribosyltransferase activity (b) produce active acetohydroxy acid synthase II and (c) reduce expression of the iclR and arpA gene products. Positions of the IS elements on a genome map of E. coli MG1655 are shown in FIG. 1 and Table 2 of U.S. Pat. No. 8,178,339, the contents of which are incorporated herein by reference. Insertion sequence elements which commonly occur in E. coli and which may be removed, include without limitation, IS1, IS2, IS3, IS4, IS5, IS30, IS150, IS186, IS600, IS911 and IS10. Preferably, the native parent E. coli K-12 strain is E. coli K-12 strain MG1655.

In a related embodiment, a reduced genome E. coli K-12 strain modified so as to (a) enhance orotate phosphoribosyltransferase activity (b) produce active acetohydroxy acid synthase II and (c) reduce expression of the iclR and arpA gene products and lacking one or more of the genes listed at Tables 2-20 of U.S. Pat. No. 8,178,339. In a preferred embodiment, the reduced genome E. coli K-12 strain lacks at least the following genes (identified by "b" numbers based on the designations set out in Blattner et al., Science, 277:1453-74 and in GenBank Accession No. 400096): b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-b4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, and b4455, which are the genes deleted from E. coli K-12 MG1655 to create reduced genome (or multiple deletion) strain MDS39. In another preferred embodiment, the reduced genome E. coli K-12 strain further lacks the following gene: b1786, which is the gene deleted from MDS39 to create reduced genome strain MDS40. In another preferred embodiment, the reduced genome E. coli K-12 strain further lacks the following genes: b0150-b01530, which are the genes deleted from MDS40 to create MDS41 In yet another preferred embodiment, the reduced genome E. coli K-12 strain further lacks the following gene: b2945 (endA) which is the gene deleted from MDS41 to create reduced genome strain MDS42. In still another embodiment, the reduced genome E. coli K-12 strain further lacks the following genes: b0315-b0331 and b0333-b0354, which are the genes deleted from MDS42 to create reduced genome strain MDS43. In yet another embodiment, the reduced genome E. coli K-12 strain further lacks the following genes: b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, b0502, which are the genes deleted from MDS43 to create MDS60. In yet another embodiment, the reduced genome E. coli K-12 strain further lacks the following genes: b0566-b0575, b2209, b0160-b0161, b1431-b1444, b3643, b1037-b1043, b0383, b0226-b0234, b2115-b2132, which are the genes deleted from MDS60 to create MDS69. In certain embodiments, reduced genome E. coli K-12 strain MDS41, MDS42, MDS60 or MDS69 is modified to create the modified E. coli K-12 strain of the invention.

In other embodiments, the parent *E. coli* K-12 strain that is modified to (a) enhance orotate phosphoribosyltransferase activity (b) produce active acetohydroxy acid synthase II and (c) reduce expression of the iclR and arpA gene products, lacks a functional recA gene (b2699). In one aspect, an *E. coli* K-12 strain such as MG1655 or W3110 is modified by deletion of iclR/arpA, enhancement of orotate phosphoribosyltransferase activity and restoration of acetohydroxy acid synthase II activity to produce a modified *E. coli* K-12 strain of the invention, followed by inactivation of b2699 by complete or partial deletion of the gene from the modified *E. coli* K-12 strain. In another aspect, a reduced genome *E. coli* strain such as e.g. strain MDS40, MDS41, MDS42 or MDS69 is modified by deletion of iclR/arpA, enhancement of orotate phosphoribosyltransferase activity and restoration of acetohydroxy acid synthase II activity to produce a modified *E. coli* K-12 strain of the invention followed by inactivation of b2699 by complete or partial deletion of the gene from the modified *E. coli* K-12 strain.

In other embodiments, the modified *E. coli* K-12 strain of the invention (i.e., that is modified to (a) enhance orotate phosphoribosyltransferase activity (b) produce active acetohydroxy acid synthase II and (c) reduce expression of the iclR and arpA gene products), comprises a relA gene containing any of the mutations described in U.S. Pat. No. 8,367,380, the contents of which are incorporated herein by reference.

In other embodiments, the modified *E. coli* K-12 strain of the invention (i.e., that is modified to (a) enhance orotate phosphoribosyltransferase activity (b) produce active acetohydroxy acid synthase II and (c) reduce expression of the iclR and arpA gene products), comprises one or more non-functional genes selected from the group consisting of the genes encoding Pol II, Pol IV and Pol V, as described in WIPO Publication No. 2013/059595, the contents of which are incorporated herein by reference. In one embodiment, the modified *E. coli* K-12 strain bacteria has non-functional polB (b0060, coordinates 63429-65780 on the *E. coli* K12 MG1655 genome), dinB (b0231, coordinates 250898-251953 on the MG1655 genome) and umuDC genes (b1183-b1184, coordinates 1229990-1231667 on the MG1655 genome). Preferably, the gene(s) are rendered inactive by complete or partial deletion.

The modified *E. coli* K-12 strain bacteria of the invention may comprise a heterologous nucleic acid encoding a polypeptide. The polypeptide may be a therapeutic protein such as insulin, an interleukin, a cytokine, a growth hormone, a growth factor, erythropoietin, a colony stimulating factor, interferon, or an antibody. The heterologous nucleic acid may be placed within a vector such as a plasmid and operatively linked to a promoter and optionally additional regulatory sequences.

The modified *E. coli* K-12 strain bacteria of the invention (modified so as to (a) enhance orotate phosphoribosyltransferase activity (b) produce active acetohydroxy acid synthase II and (c) reduce expression of the iclR and arpA gene products) may be used to produce polypeptides. Briefly a bacterium of the invention comprising a heterologous nucleic acid encoding a polypeptide operatively linked to an expression control sequence, as described above, may be incubated under conditions sufficient to allow expression of the polypeptide product. Increased production of polypeptide in modified *E. coli* K-12 strain bacteria of the invention can be achieved compared to *E. coli* K-12 strain bacteria without the modifications (such as compared to wild type MG1655 or W3110 or compared to *E. coli* K-12 strain bacteria with the same genetic background but without the modifications). In addition, the increased number of modified *E. coli* K-12 strain bacteria produced in a culture over the number of unmodified *E. coli* K-12 bacteria that can be produced under identical fermentation conditions increases the production of polypeptide. The increased production of polypeptide may be particularly significant in fed batch fermentations using minimal media. In one aspect, the polypeptide is a single-chain antibody.

Recombinant proteins may be expressed in the periplasm or cytoplasm. The expression of proteins in the periplasm is routinely used for industrial use and has been reviewed in Hanahan, J. Mol. Biol., 166:557-580 (1983); Hockney, Trends Biotechnol., 12:456-632 (1994); and Hannig et al., Trends Biotechnol., 16:54-60 (1998), each of which is incorporated herein by reference. Recombinant proteins may be produced in the periplasm by expressing fusion proteins in which they are attached to a signal peptide that causes secretion into the periplasmic space. There, the signal peptide may be cleaved off by specific signal peptidases. The protein transported into the periplasmic space may be biologically active.

The recombinant protein may be co-expressed with chaperones/disulfide-bond forming enzymes, which may provide proper folding of the recombinant protein. Nucleic acid sequences of such proteins useful for periplasmic expression of recombinant protein include, without limitation, those described in U.S. Pat. Nos. 5,747,662; 5,578,464 and 6,022,952, each of which is incorporated herein by reference.

The modified *E. coli* K-12 strain bacteria of the invention are also particularly useful as hosts for amplifying nucleic acids. Briefly a bacterium of the invention comprising a heterologous nucleic acid may be incubated under conditions sufficient to allow replication of the nucleic acid product. Increased production of nucleic acids in modified *E. coli* K-12 strain bacteria of the invention can be achieved compared to *E. coli* K-12 strain bacteria without the modifications (such as compared to wild type MG1655 or W3110 or compared to *E. coli* K-12 strain bacteria with the same genetic background but without the modifications). In addition, the increased number of modified *E. coli* K-12 strain bacteria produced in a culture over the number of unmodified *E. coli* K-12 bacteria that can be produced under identical fermentation conditions increases the production of the desired nucleic acid molecules. The increased production of nucleic acid molecules may be particularly significant in fed batch fermentations using minimal media.

Example 1

Production of Modified *E. coli* K Strains

The genomic sequence of *E. coli* K-12 strain MG1655 was compared to that of *E. coli* B strains BL21/DE3 and REL606 in order to correlate the phenotypic differences between B strains and K strains to specific genetic features. An alignment of *E. coli* strain K-12 MG1655 and B strain BL21/DE3 revealed that 1,415 of the approximately 4,400 genes present in MG1655 are identical. Of the remaining genes, 464 genes contain insertions or deletions, 2,106 genes contain single base changes of which 1,249 result in non-synonymous changes at the amino acid level. The remainder is composed of broken or missing genes, generally clustered within large scale features such as remnant prophage. A similar alignment between K strain MG1655 and B strain REL606 revealed 1,423 identical genes, 472 genes containing insertion or deletions and 2,128 genes with single base changes of which 1,277 result in non-synonymous changes at the amino acid level. To provide perspective, alignment of the two B strains BL21/DE3 and REL606 indicates that there are 4078 identical genes and only 26 genes contain insertions or deletions. There are 105 genes with single base changes of which 66 result in non-synonymous changes. Thus, as expected, the differences between the B strain and K-12 strain genomes are much more significant than the differences between the two B strains.

The large number of genetic differences between strains was narrowed by focusing on those genes and gene products that are most likely to affect growth properties under industrial fermentation conditions. A recent report correlating genotype and phenotype differences between E. coli B and K-12 strains identifies a number of genes as candidates for improving K-12 strain growth [Yoon et al., Genome Biology 13:R37 (2012)]. Unfortunately, much of the data reported by Yoon et al., derives from cultures grown in rich (Luria Broth) media and is not relevant to industrial fermentations. Although LB media is commonly used in the research laboratory, it is not favored in large scale industrial fermentations for two opposing reasons. For production of low value commodities such as bulk amino acids for the feed industry, LB is simply too expensive; whereas for high value pharmaceutical or fine chemical production, LB media is either banned for containing animal by-products or is too chemically complex and complicates product recovery. Thus, in virtually all large-scale industrial fermentations minimal media compositions are preferred.

Three separate genetic modifications were identified as especially promising to improve the ability of E. coli K-12 strain to grow on minimal media. The modifications represent an attempt to impart B strain like growth characteristics to E. coli K-12 strains, which are thought to be inferior production hosts compared to B strains, thereby creating a strain combining features of B and K-12 strains optimal for use in the production of proteins and genetic engineering. The genetic modifications were made to reduced genome E. coli strains derived from the canonical E. coli K-12 strain MG1655. These reduced genome strains exhibit typical K-12 strain characteristics when grown in minimal media such as metabolite overflow, anoxic cycling and partial starvation for pyrimidines and other metabolites. Thus, these strains are good candidates for improvement by selective incorporation of B strain genetic differences.

Reduced genome strain MDS39 was produced as described in International Patent Publication No. WO 2003/070880, which is incorporated herein by reference. Briefly, a series of reduced genome strains (MDS01-MDS39) were produced by making a series of 39 cumulative deletions (approximately 14.1% of the genome) of nucleic acid sequences from the parental strain E. coli MG1655.

Hybridization to genome scanning chips (NimbleGen Systems, Madison, Wis.) containing the K-12 sequence and all sequences in the IS database revealed that MDS39, the first strain designed to lack all IS elements, unexpectedly contained additional copies of an IS element that had translocated to new locations during its production. These IS elements were deleted to produce MDS40. The fhuACDB (the tonA locus) was deleted from MDS40 to produce MDS41. The location and function of each cumulative deletion made to produce MDS01-MDS41 can be found at Table 2 of U.S. Pat. No. 8,178,339, the entire content of which is incorporated herein by reference. The endA gene was then deleted from MDS41 to produce MDS42. Twenty-seven additional nucleic acid deletions were made in MDS42 to create MDS69, the location and function of which can be found at Table 2 of U.S. Pat. No. 8,178,339.

The following modifications were made to MDS42 and MDS69 both separately and in combination: (i) deletion of the iclR and arpA genes (ii) deletion of the rph gene, (iii) correction of the ilvG frameshift mutation and (iv) deletion of the recA gene. The modifications were verified by polymerase chain reaction (PCR) and sequencing using flanking primers and later confirmed by full genome sequencing.

The iclR and arpA genes were deleted from the genome of MDS42 and MDS69 bacteria using a suicide plasmid-based method as described in U.S. Pat. No. 6,989,265 and Feher et al., Methods Mol. Biol., 416:251-259 (2008). Briefly, two regions of sequence immediately upstream and downstream of the iclR and arpA genes were initially amplified from genomic DNA separately and then, in a secondary amplification recombined by annealing common sequence encoded within the o-DAF 57 OL primers to form the desired deletion junction. The initial amplifications used primers SCG803 (5'-AATGGTGATGTTGGTGTT-TACGCTGC-3') (SEQ ID NO:1) paired with o-DAF57 OL-L (5'-GCATCTGTGGTAAAAACCCTCGATACATT-GCGGAGAAAAATT-3') (SEQ ID NO:2) and SCG362 (5'-GCCCCAGCGCACAGTTCAGG-3') (SEQ ID NO:3) paired with o-DAF57 OL-R (5'-AATGTATCGAGGGTTTT-TACCACAGATGCGTTTATGCCAGTATG-3') (SEQ ID NO:4). The individual PCR products were recombined by annealing the common sequence encoded within the o-DAF 57 OL primers to form the desired deletion junction and amplified with primers o-DAF57 L spe (5'-ATGAACTAGT-TGTGATTCGCCATCTTTATATTGAGCG-3') (SEQ ID NO:5) and o-DAF57 R ecoR (5'-ATGAGATTCTCCACCA-GCGCTTTGGTGGAC-3') (SEQ ID NO:6) to produce a single combined fragment encompassing the deletion junction. This combined fragment was cloned into the suicide plasmid to form plasmid pSG5483. After insertion of pSG5483 into the chromosome and resolution of the cointegrant, the deletion was confirmed by PCR analysis of genomic DNA from isolated colonies using primers SCG803 and SCG362. A PCR product of 1,614 base pairs indicated deletion of the targeted genes, whereas a PCR product of 5,024 base pairs indicated retention of intact iclR/arpA. Fidelity of the deletion was confirmed by sequencing the deletion PCR products to ensure the expected sequence was present.

The rph gene was deleted from the genome of MDS42 and MDS69 bacteria in order to enhance orotate phosphoribosyltransferase activity. The transcriptional levels of the downstream pyrE gene were increased by removing the polarity caused by the frameshift within the rph gene. Briefly, following the deletion strategy described above, two regions of sequence upstream and downstream of the rph gene were initially amplified separately and then in a secondary amplification recombined by annealing the common sequence encoded within the o-DAF rph primers to form the desired deletion junction. The initial amplifications used primers SCG3679 (5'-GCTCATACTAGTGCGCCT-GCGTCTGATTGTGTTG-3') (SEQ ID NO:7) paired with o-DAF rph L (5'-GTTTCAAGCCGGAGATTTCAATAT-GAAACCATATCAGCGCCAG-3') (SEQ ID NO:8) and SCG3680 (5'-CTTACGAAGCTTCGGCATATGGGAGCG-GACTTTG-3') (SEQ ID NO:9) paired with 0-DAF rph R (5'-CTGATATGGTTTCATATTGAAATCTCCGGCTT-GAAACAAATGT-3') (SEQ ID NO:10). The combined annealed fragments were then amplified with primers SCG3679 and SCG3680 and the resulting PCR product encoding the deletion junction was cloned into the suicide plasmid to form plasmid pSG5787. After insertion of pSG5787 into the chromosome and resolution of the cointegrant, the deletion was confirmed by PCR analysis of isolated colonies using primers SCG3682 (5'-CTCGCG-CATCTGCTCAATCAACACTT-3') (SEQ ID NO: 11) and SCG3681 (5'-GAAAAGGAACCGTCGCGAG-GAAATACT-3') (SEQ ID NO:12). A PCR product of 2,224 base pairs indicated deletion of the rph gene, whereas a PCR product of 3,005 base pairs indicated retention of intact rph. Fidelity of the deletion was confirmed by sequencing the deletion PCR products to ensure the expected sequence was present.

The frameshift mutation in the ilvG gene sequence (deletion of GT at positions 983 and 984) was modified in MDS42 and MDS69 bacteria so that full length, functional acetohydroxy acid synthase II was expressed from the modified ilvG gene. In this case, the frameshift was reversed by insertion of an AT dinucleotide at position 982 by amplification of the ilvG region of the chromosome. In the procedure two fragments encoding overlapping sequences upstream and downstream of the insertion point and including the modification were initially amplified separately and then in a secondary amplification recombined by annealing the common sequence encoded within the o-DAF ilvG primers to form the desired AT insertion junction. The initial amplifications used primers SCG3684 (5'-CTGCTA-ACTAGTGCGGCTATCGGTTATGCTCGTGCTAC-3') (SEQ ID NO: 13) paired with o-DAF ilvG L (5'-CTGCCA-GTCATATTGATTTAACGGCTGCTGTAATGCTGG-TAAC-3') (SEQ ID NO:14) and SCG3685 (5'-GGCATA-GAAGCTTGCTCAGGCGCGGATTTGTTGTG-3') (SEQ ID NO:15) paired with o-DAF ilvG R (5'-CAGCAGCCGT-TAAATCAATATGACTGGCAGCAACACTGCGCGC-3') (SEQ ID NO:16). The combined and annealed fragments were then amplified with primers SCG3684 and SCG3685 and the resulting insertion template cloned into the suicide plasmid to form plasmid pSG5855. After insertion of pSG5855 into the chromosome and resolution of the cointegrant, the deletion was confirmed by screening candidate colonies for their ability to grow on minimal media supplemented with 0.2% glucose and 40 µg/ml valine. Fidelity of the deletion was confirmed by sequencing the ilvG locus of the valine resistant clones to ensure the expected sequence was present.

Finally, MDS42 and MDS69 bacteria were modified such that they harbored all three of these modifications (deletion of iclR, arpA and rph genes and correction of the ilvG frameshift mutations). The deletions were assembled sequentially to produce each meta strain derivative, beginning with deletion of iclR/arpA, followed by deletion of rph and then repair of ilvG. In a final step, the recA gene (the recA1819 allele) was inactivated by deletion in the MDS42 and MDS69 meta strains to form recA versions of the strains. The deletion was produced by the same two step procedure described for the iclr/arpA and rph gene deletions using primers SCG251 (5'-GAATCCAAGCACTAGT-CACAGCACCCATTACGCAATGGC-3') (SEQ ID NO:17) paired with DAF recA L (5'-CATCTACAGAGAAATCATA-CAGTATCAAGTGTTTTGTAGAAATTGT-3') (SEQ ID NO:18) and SCG252 (5'-GGCCCTCGAGAAGCTTC-TATGGAAAAAGTCGAGAAACGCCTGAC-3') (SEQ ID NO:19) paired with DAF recA R (5'-CACTTGATACTG-TATGATTTCTCTGTAGATGATAGCGAAGGCGTA-3') (SEQ ID NO:20). The combined and annealed fragments were then amplified with primers SCG251 and SCG252 and the resulting insertion template cloned into the suicide plasmid to form plasmid pSG2857. After insertion of pSG2857 into the chromosome and resolution of the cointegrant, the deletion was confirmed by PCR analysis of isolated colonies using primers SCG225 (5'-GCCTGCT-GCGTCTGGATGTTGG-3') (SEQ ID NO:21) and SCG226 (5'-ACTGGTTCATCCCGGCGTTGGTA-3') (SEQ ID NO:22). A PCR product of 1,688 base pairs indicates deletion of the recA gene, whereas a PCR product of 2,767 base pairs indicates retention of intact recA. Fidelity of the deletion was confirmed by sequencing the deletion PCR products to ensure the expected sequence was present. Recombinational mutagenesis is facilitated by RecA, therefore strains containing the recA1819 deletion mutation are not suitable for further deletion mutagenesis by the methods described in U.S. Pat. No. 6,989,265 and Feher et al., Methods Mol. Biol., 416:251-259 (2008).

Example 2

Growth Characteristics of the Modified *E. coli* K Strains

The effects of each modification on growth and fermentability (i.e. fermentation productivity) were tested separately in MDS42, MDS69, MDS42recA and MDS69recA bacteria. To test the effects of the modifications an objective method for measuring "fermentability" was designed to control for the effects of variables such as inconsistent fermentation conditions and media composition. According to this test, the fermentability of different strains is compared by measuring the maximum optical density (OD) to which the cells can be grown in a standardized fed batch fermentation (in the present case, ten liter fed batch fermentation at 37 C with minimal salts medium (a slightly modified Korz medium with fully-defined minimal salts with trace elements). Glucose was added to the batch phase to 0.5% and the cell growth rate was limited by feeding with glucose at a constant exponential feed rate of 0.3 $hr^{-1}$ during the fed batch phase. Dissolved oxygen is maintained at 40% throughout the fermentation and pH is kept constant at 6.9 by addition of ammonia. Each *E. coli* contained an uninduced protein expression plasmid with a kanamycin resistance gene and kanamycin was added to the media to mimic the stress of a manufacturing situation. As cells grow to higher and higher density, a point is eventually reached where the cells metabolic capacity to sustain the growth rate is exceeded and the cells can no longer consume glucose. In a fed batch fermentation, glucose is introduced into the fermenter at a particular feed rate. When the cells can no longer consume the glucose as quickly as it is fed into the vessel, the residual glucose concentration increases rapidly, resulting in a so-called glucose spike. A glucose spike indicates the fermentation has reached its maximum limit. The highest OD that can be reached before a glucose spike for a given strain under standard conditions defines the fermentability of that strain. Glucose was monitored and if a glucose spike was observed, the fermentability was taken as the OD at which this happened. If no glucose spike was observed and the cells were induced by adding inducer and lowering the feed rate, the OD at induction served as a lower bound of the fermentability of the strain. Increases in OD past induction were not counted in determining fermentability. If the run was terminated by experimental exigencies such as running out of feed, equipment failure or exceeding the capacity to deliver oxygen or cooling, the OD at which these events occurred was also used as a minimal estimate of fermentability.

The effects of the single modifications on the growth and fermentability of MDS42, MDS69, MDS42recA and MDS69recA were not significant. Surprisingly, however, when all three modifications were made to MDS42, MDS69, MDS42recA and MDS69recA, fermentability was significantly increased. As can be seen from FIG. 1, all strains containing the modifications exhibit significantly improved fermentability characteristics relative to the unmodified parent MDS42, MDS69, MDS42recA and MDS69recA strains and compared to both a wild type K-12 strain (MG1655) and a wild type B strain (BL21(DE3)). In addition, FIG. 1 also shows fermentability of strain MDS42recA(Lowmut), an MDS42recA derivative lacking the error prone polymerases encoded by the dinB, umuDC and polB genes.

MDS42recA(Lowmut) is described in International Patent Publication No. WO 2013/059595, which is incorporated herein by reference. The doubling time and Mu in minimal medium of modified K strains (MDS42 meta, MDS42 Meta loMut, MDS42 meta recA, and MDS42 meta LoMut recA) compared to their unmodified parent strains are illustrated in Table 1 below:

TABLE 1

| recA+ | MDS42 | SG2707<br>MDS42<br>DT = 74.4 min;<br>Mu = 0.56 hr$^{-1}$ (#701) | SG6265<br>MDS42 meta<br>DT = 54.8 min;<br>Mu = 0.76 (#1067) |
|---|---|---|---|
| | LOmut | SG6261<br>MDS42 LoMut<br>DT = 77.1 min;<br>Mu = 0.54 (#1146) | SG6786<br>MDS42 Meta loMut<br>DT = 58.0 min;<br>Mu = 0.72 (#1143) |
| recA− | MDS42 | SG3100<br>MDS42 recA<br>DT = 75.5 min;<br>Mu = 0.55 (#822) | SG6328<br>MDS42 meta recA<br>DT = 62.5 min;<br>Mu = 0.67 (#1068) |
| | LOmut | SG6262<br>MDS42 LoMut recA<br>DT = 83.8 min;<br>Mu = 0.50 (#1115) | SG6787<br>MDS42 meta LoMut recA<br>DT = 63.9 min;<br>Mu = 0.65 (#1141) |

The metabolic mutations (correction of the ivlG frameshift mutations and deletion of the rph, iclR and arpA genes) significantly boosted the fermentability in all strains tested, rendering them surprisingly more productive than the strains lacking the metabolic mutations (meta). The improved productivity of the strains is demonstrated in the increase in plasmid and protein production described below.

Example 3

Nucleic Acid Production from the Modified *E. coli* K Strains

Improved production of nucleic acids is shown in Table 2. Strains MDS42recA (fermentation No. 141) and MDS42 meta recA (fermentation No. 139) were each transformed with a recombinant plasmid gWIZ™ (Genlantis, San Diego, Calif. 92121). Each strain was grown in a ten liter fermenter in minimal media as described above. Cells were harvested and plasmid DNA prepared by alkaline lysis and quantitated by spectrophotometric methods (UV absorbance 260/280). Percent plasmid as supercoil was determined by gel electrophoresis and scanning densitometry. Representative plasmid recoveries from these fermentations are shown in Table 2 below.

TABLE 2

| Strain | OD at Max pDNA | Max pDNA yield | percent supercoil |
|---|---|---|---|
| MDS42 recA | 190 | 495 mg/L | not measured |
| MDS42 meta recA | 227 | 683 mg/L | 90% |

Example 4

Protein Production from the Modified *E. coli* K Strains

Next, the usefulness of the modified *E. coli* strains as protein production hosts was tested. Strains T69recA meta and T69 meta (parent strains MDS69recA and MDS69, respectively, each modified to correct the ivlG frameshift mutation and delete the rph, iclR and arpA genes), were transformed with a plasmid expressing the human gelsolin gene from the IPTG-inducible promoter pT5/lac (referred to as pT5lacSO-GSN). Plasmid pT5lacSO-GSN comprises a bacterial promoter similar to the $P_{AI/o5}$ promoter described in Lanzer and Bujard, Proc. Natl. Acad. Sci. U.S.A. 85:8973-8977 (1988). The sequence of human gelsolin is known (see e.g. GenBank Accession No. NM_000177). The plasmid backbone, including the pUC origin of replication, the kanamycin resistance gene and the lacI repressor gene is derived from pJ441-01, available from DNA2.0, Menlo Park, Calif. 94025.

The transformed strains were subjected to batch feed fermentation at 37 C to an $OD_{600}$ of about 8 followed by exponential feed at Mu=0.3 to an $OD_{600}$ of about 300 in the case of T69recA meta (the fermentability of strain T69recA meta as determined above), after which production of the gelsolin protein product was induced by addition of IPTG at constant glucose feed. Gelsolin, an 85 kD soluble protein that is produced in the cytoplasm of the bacteria was purified by microfluidization of the bacteria followed by anion exchange chromatography. Protein yield was assessed by gel electrophoresis and compared to that following fed batch fermentation of the unmodified parent strain (T69/MDS69). As can be seen from Table 2 below, protein yield was significantly increased in the modified strain. Similar results were obtained using glycerol in the feed media.

TABLE 3

| Strain | OD max | IPTG at OD | Protein (g/l) |
|---|---|---|---|
| T69recA | 188 | 100 μM | 25.6 ± 1.7 |
| T69recA meta | 276.5 | 75 μM | 35.6 |
| T69recA meta | 285 | 75 μM @ 206.5 OD | 35.8 |
| T69recA meta | 284.5 | 75 μM @ 230 OD | 32 |
| T69recA meta | 331.3 | 75 μM @ 306.5 OD | 42.8 |

Together, Tables 2 and 3 in conjunction with the range of fermentability typical of unmodified *E. coli* K-12 (MG1655) and B (BL21/DE3) strains shown in FIG. 1, demonstrate the presence of the metabolic mutations (correction of the ivlG frameshift mutation and deletion of the rph, iclR and arpA genes) in *E. coli* K-12 cell lines confers improved growth rates (faster doubling times, higher Mu) resulting in higher cell densities and improved production of nucleic acids and proteins.

Example 5

Protein Production from Stationary Phase Modified E. coli K Strains

Figure 2:
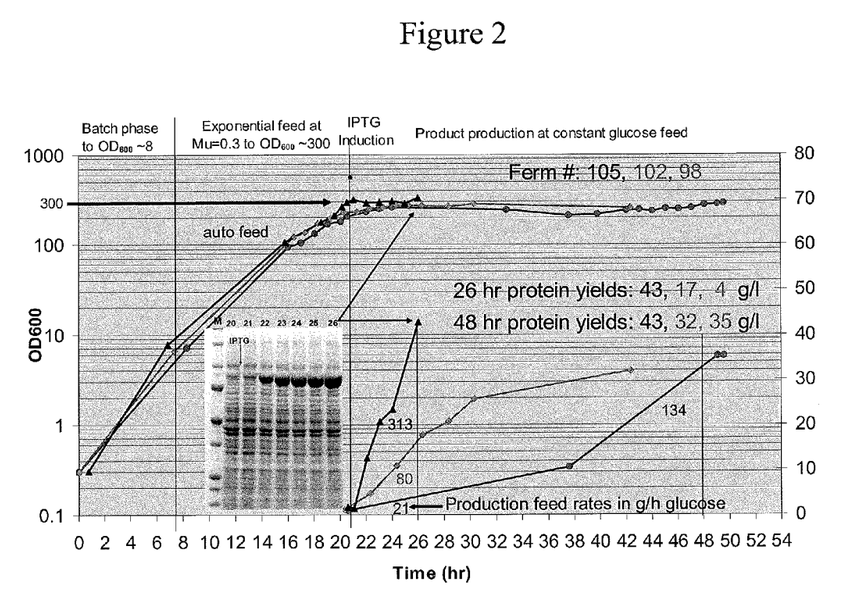
Figure 3:
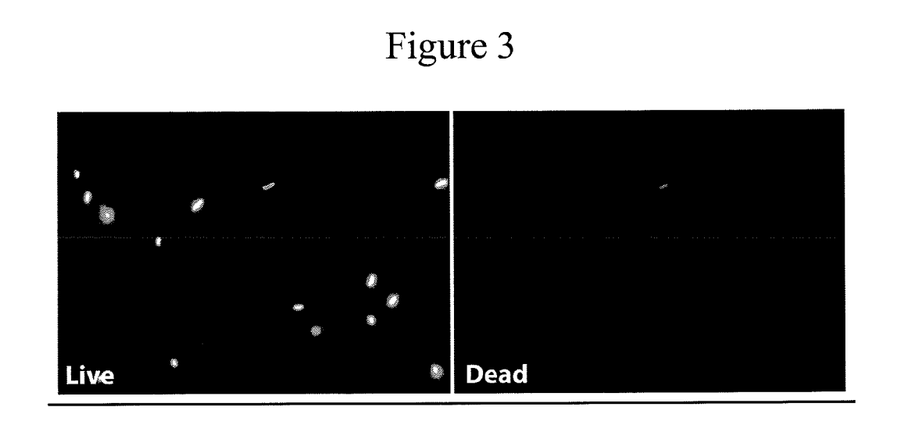

FIG. 2 illustrates the ability of the modified *E. coli* strains to produce protein in stationary phase without concomitant production of biomass. The main plot in the Figure is a growth curve ($OD_{600}$ by time in hours). The inset plot relates productivity (g/L product protein by time in hours). The left axis relates $OD_{600}$ and the right axis is g/L product protein. The additional inset graphic is a gel displaying the production of protein at the indicated time points. The concentration of product protein is estimated from the gel and from total protein measurements.

In each of the fermentations shown in FIG. 2 the fermentation reaches stationary phase at about 21 hours, at which point transcription of the recombinant protein is induced by addition of IPTG. Upon induction, the feed rate of glucose is varied among the three cultures (Ferms. No. 105, 102 and 98 received 313, 80 and 21 g/h glucose, respectively). Interestingly, rather than resuming growth by converting the newly available glucose to biomass, the glucose is converted almost exclusively to product protein.

---

What is claimed is:

1. A modified *Escherichia coli* K-12 strain, wherein said strain is modified so as to:
   (a) enhance orotate phosphoribosyltransferase activity by the introduction of a mutation which complements a native −1 frameshift mutation in the Ribonuclease PH (rph) gene or by deletion of the rph gene
   (b) produce active acetohydroxy acid synthase II by the introduction of a mutation which complements a native −2 frameshift mutation in the valine-insensitive acetohydroxy synthase II large subunit (ilvG) gene; and
   (c) reduce expression of the isocitrate lyase (iclR) and ankyrin repeat protein A (arpA) gene products by deletion of all or part of the iclR and arpA genes.

2. The modified *E. coli* K-12 strain of claim 1, wherein the strain lacks a functional recombination protein A (recA) (b2699) gene.

3. The modified *E. coli* K-12 strain of claim 1, wherein the modified *E. coli* K-12 strain is a modified MG1655, W3110, DH1, DH10B, DH5α, Invα, Top10, Top10F, JM103, JM105, JM109, MC1061, MC4100, XL1-Blue, EC100, BW2952, or EC300 strain.

4. The modified *E. coli* K-12 strain of claim 3, wherein the modified *E. coli* K-12 strain is a modified *E. coli* K-12 strain MG1655 or W3110 strain.

5. The modified *E. coli* K-12 strain of claim 1, wherein the modified *E. coli* K-12 strain is genetically engineered to be from about 2% to about 25% smaller than *E. coli* strain MG1655.

6. The modified *E. coli* K-12 strain of claim 5, wherein the modified *E. coli* K-12 strain is genetically engineered to be about 14.1% to about 25% smaller than *E. coli* strain MG1655 by deletion of at least the genes deleted from reduced genome *E. coli* strain MDS42.

7. The modified *E. coli* K-12 strain of claim 5, wherein the modified *E. coli* K-12 strain is genetically engineered to be about 20.3% to about 25% smaller than *E. coli* strain MG1655 by deletion of at least the genes deleted from reduced genome *E. coli* strain MDS69.

8. The modified *E. coli* K-12 strain of claim 6, wherein the modified *E. coli* K-12 strain is produced by modifying reduced genome *E. coli* strain MDS42.

9. The modified *E. coli* K-12 strain of claim 1, wherein the strain encodes a relaxed (relA) gene having at least one point mutation at position 547 or 548 of the coding sequence of the relA gene, wherein the mutation is selected from one or more of: a G→A mutation at position 547, a G→T mutation at position 547, a C→G mutation at position 548, or a C→T mutation at position 548.

10. The modified *E. coli* K-12 strain of claim 1, wherein the strain lacks a functional DNA polymerase IV (dinB)

(b0231) gene and optionally lacks functional DNA, polymerase V (umuDC) (b1183-b1184) and/or DNA polymerase II (polB)(b0060) genes.

11. The bacterium of claim 1 comprising a heterologous nucleic acid.

12. The bacterium of claim 11, wherein said heterologous nucleic acid comprises a nucleic acid encoding a polypeptide operatively linked to an expression control sequence.

13. The modified *E. coli* K-12 strain of claim 9, wherein the strain lacks a functional dinB (b0231) gene and optionally lacks functional umuDC (b1183-b1184) and/or polB (b0060) genes.

14. The modified *E. coli* K-12 strain of claim 1, wherein (i) the strain is modified to enhance orotate phosphoribosyltransferase activity by deletion of the rph gene (ii) the strain is modified to produce active acetohydroxy acid synthase 11 by the introduction of a mutation which complements a native −2 frameshift mutation in the ilvG gene; and (iii) the strain is modified to reduce expression of the iclR and arpA gene products by deletion of the iclR and arpA genes.

15. The modified *E. coli* K-12 strain of claim 14, wherein the strain lacks a functional recA (b2699) gene.

16. The modified *E. coli* K-12 strain of claim 14, wherein the strain lacks a functional dinB (b0231) gene and optionally lacks functional umuDC (b1183-b1184) and/or polB (b0060) genes.

17. The modified *E. coli* K-12 strain of claim 14, wherein the unmodified parent *E. coli* strain is a reduced genome *E. coli* bacterium having deleted therefrom at least the genes deleted from reduced genome *E. coli* strain MDS42.

18. The modified *E. coli* K-12 strain of claim 14, wherein the unmodified parent *E. coli* strain is a reduced genome *E. coli* bacterium having deleted therefrom at least the genes deleted from reduced genome *E. coli* strain MDS69.

19. A method for producing a polypeptide comprising incubating the bacterium of claim 12 under conditions suitable for expressing the polypeptide and collecting the polypeptide.

* * * * *